(12) United States Patent
Gebauer et al.

(10) Patent No.: US 9,675,947 B2
(45) Date of Patent: Jun. 13, 2017

(54) MIXING SYSTEM (71) Applicant: GE HEALTHCARE BIO-SCIENCE AB, Uppsala (SE)

(72) Inventors: Klaus Gebauer, Uppsala (SE); Patrick Jonsson, Uppsala (SE); David Ronnholm, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 265 days.

(21) Appl. No.: 14/384,195

(22) PCT Filed: Mar. 14, 2013

(86) PCT No.: PCT/SE2013/050238
§ 371 (c)(1),
(2) Date: Sep. 10, 2014

(87) PCT Pub. No.: WO2013/137812
PCT Pub. Date: Sep. 19, 2013

(65) Prior Publication Data
US 2015/0029815 A1    Jan. 29, 2015

(30) Foreign Application Priority Data

Mar. 16, 2012  (SE) .................................. 1250248-0

(51) Int. Cl.
*B01F 5/06*         (2006.01)
*B01F 13/00*        (2006.01)
(Continued)

(52) U.S. Cl.
CPC .............. *B01F 13/00* (2013.01); *B01F 15/06* (2013.01); *C12M 23/14* (2013.01); *C12M 23/28* (2013.01);
(Continued)

(58) Field of Classification Search
CPC ....................................................... B01F 15/06
(Continued)

(56) References Cited

U.S. PATENT DOCUMENTS 1,376,016 A  *  4/1921  Howell .................. A23G 9/163
                                                    165/94
5,143,449 A  *  9/1992  Faccia .................... A01D 90/10
                                                    280/1
(Continued)

FOREIGN PATENT DOCUMENTS

CA           2760728 A       11/2010
WO      WO2009041021 A1       4/2009

OTHER PUBLICATIONS

Office Action issued in corresponding CN Application 201380014400.1, filed Mar. 14, 2013 (Nov. 25, 2015).
(Continued)

*Primary Examiner* — David Sorkin
(74) *Attorney, Agent, or Firm* — Wood IP LLC (57) ABSTRACT

The present invention relates to a mixing system comprising a vessel (1) for housing a disposable fluid mixing bag (2), which vessel (1) comprises a base (3) supporting the fluid mixing bag (2) and a sidewall (4) extending vertically upwards from the base (3). The sidewall (4) of the vessel comprises a door opening (5) which is closable by a sliding door (6). The system with the sliding door provides an easy access to the inside of the vessel (1) in a space saving manner.

19 Claims, 4 Drawing Sheets

(51) Int. Cl.
*C12M 1/00* (2006.01)
*C12M 3/00* (2006.01)
*B01F 15/06* (2006.01)
*B01F 15/00* (2006.01)

(52) U.S. Cl.
CPC ............ *C12M 23/48* (2013.01); *C12M 23/52* (2013.01); *B01F 15/0085* (2013.01); *B01F 15/00792* (2013.01); *B01F 2015/061* (2013.01); *B01F 2015/062* (2013.01)

(58) Field of Classification Search
USPC .............. 220/495.01, 495.08, 495.11, 345.1; 366/149
See application file for complete search history.

(56) References Cited

U.S. PATENT DOCUMENTS

| | | | |
|---|---|---|---|
| 5,423,448 A * | 6/1995 | Pedigo | B65F 1/122 220/345.1 |
| 5,863,122 A * | 1/1999 | Tamminga | A01K 5/004 241/101.761 |
| 6,267,461 B1 * | 7/2001 | Dunagan | A63B 47/002 220/345.1 |
| 7,992,846 B2 | 8/2011 | Terentiev et al. | |
| 2003/0226857 A1 | 12/2003 | Bibbo et al. | |
| 2011/0062261 A1 | 3/2011 | Milam et al. | |
| 2011/0207218 A1 | 8/2011 | Staheli et al. | |
| 2011/0310696 A1 | 12/2011 | Goodwin et al. | |
| 2012/0037637 A1 * | 2/2012 | Beyda | B65F 1/06 220/495.11 |
| 2012/0100605 A1 | 4/2012 | Kauling et al. | |

OTHER PUBLICATIONS

JP Office Action issued Nov. 1, 2016 for corresponding JP Application No. 2015-500395.

* cited by examiner

MIXING SYSTEM

CROSS-REFERENCE TO RELATED APPLICATIONS

This application is a filing under 35 U.S.C. 371 of international application number PCT/SE2013/050238, filed Mar. 14, 2013, published on Sep. 19, 2013 as WO 2013/137812, which claims priority to application number 1250248-0 filed in Sweden on Mar. 16, 2012.

TECHNICAL FIELD

The present invention relates to a technical field of mixing systems comprising a vessel for housing a disposable fluid mixing bag, which vessel comprises a base supporting the fluid mixing bag and a sidewall extending vertically upwards from the base.

BACKGROUND

Single-use or disposable systems are rapidly increasing in biopharmaceutical industry due to the flexibility and cost-effectiveness of such systems. Disposable components in the systems are presterilized and qualified to regulatory requirements. Disposable systems are easy to adapt to different production purposes and it is easy and inexpensive to change a product line while good process reliability is at least maintained, if not even improved.

There are several kinds of mixing systems in which disposable containers or bags may be used. One type of such mixing system is a bioreactor in which cells or microorganisms can grow. Mixing systems are also used to prepare for example buffer and media. The mixing systems may comprise a vessel which houses a disposable bag or container. The vessel may have a form of a cylinder, for example substantially circular cylinder. The bag is placed inside the vessel in an accurate manner so that for example different pipelines, mixers and sensors can be connected to the bag properly and accurately. US2011/0310696 shows a mixing system of this kind.

To be able to place a disposable bag inside a vessel in an accurate manner, an easy access inside the vessel is important. The vessels may vary in size and can be adapted for bags of from about 20 liters up to about 2000 liters. Especially large mixing vessels housing a bag of the disposable type require a very large floor area, which may be a limiting factor. Therefore, there is a need for an arrangement that provides an easy access to the inside of the vessel in a space-saving manner.

SUMMARY OF THE INVENTION

The present invention provides a mixing system of the type which includes a vessel for housing a disposable fluid mixing bag or container and which provides for an easy access inside the vessel in a space saving manner. The present invention also provides for a safe access to the inside the vessel so that a risk for damage of the disposable bag is minimized. The present invention also provides for an easy and space saving heating/cooling arrangement for the vessel. Further advantages of the present invention will be apparent from the description below.

The present invention relates to a mixing system comprising a vessel for housing a disposable fluid mixing bag, which vessel comprises a base supporting the fluid mixing bag and a sidewall extending vertically upwards from the base. The sidewall of the vessel comprises a door opening which is closable by a sliding door. The system with the sliding door provides for an easy access inside the vessel in a space saving manner.

The door opening may have a height of at least 30%, such as at least 50% of the height of the sidewall, preferably at least 80% and most preferably 100 of the height of the side wall, or alternatively 30-80% of the height of the sidewall. The higher the door opening, the easier the access is inside the vessel.

The sliding door is preferably slidingly suspended to an upper part of the vessel. The vessel is preferably a circular cylinder when the door is in its closed position. The upper part of the vessel may comprise an upper annular element to which the door is slidingly suspended. The upper annular element provides a simple and reliable mounting for the door suspension. Through the upper annular element it can be assured that the door can slide without a contact with the sidewall when the door is opened.

The door may comprise a suspension means comprising a guiding element for slidingly suspending the door to the annular element. The guiding element guides the door in the sliding movement, e.g. when the door is closed and/or opened in a simple manner. The upper annular element preferably comprises a track or a rail in which the guiding element, which can be a pin, can slide, whereby a simple suspension structure with sliding arrangement for the door can be obtained.

The door may comprise suspension means on both sides of the door to provide a sufficient and stable suspension which is important especially for large vessels having heavy doors. The upper annular element comprises a track or a rail for each of the suspension means, respectively.

The tracks may comprise an arcuate end portion which is closer to the diametrical center of the vessel than the remaining portion of the track. When the door is opened from its closed position, the door then moves radially outwards in relation to the diametrical center of the vessel, so that it becomes free from contact with the wall of the vessel. Through the arcuate portion, a simple solution for the radial movement of the door can be arranged.

The suspension means may further comprise a sliding means comprising a ball bearing which is arranged to slide outside the track or rail. This arrangement further improves the easy sliding movement of the door. The upper annular element may also comprise a recess in which the ball of the ball bearing can be at least partially accommodated when the door is in closed position so that the door will not be able to move unintentionally when the door is in its closed position.

Also, the lower part of the door may comprise a lower suspension means and a lower annular element on the vessel. The lower annular element may also comprise at least one track or rail to guide the lower suspension means comprising a guiding element for slidingly suspending the door to the lower annular element. The suspension means in the lower part of the door together with the annular element improve the handleability of the door, since also the lower part of the door is connected to the vessel and can be moved in a more controlled manner.

The vessel may further comprise locking means to lock the sliding door when the door is in its closed position.

Further, the interior of the vessel may comprise fastening means, such as clamp holders, to secure the mixing bag to the vessel.

The door may comprise double walls, wherein a heated or cooled liquid is arranged to flow between the double walls to warm or cool the vessel, respectively. Also, the sidewall of the vessel may further comprise double walls and a heated or cooled liquid is arranged to flow between the double walls to warm or cool the vessel. In this way space can be saved, since no separate warming or cooling arrangements for the vessel are needed.

The sidewall of the vessel may comprise an inlet and outlet for the liquid and the door may comprise an inlet and an outlet for the liquid. The outlet of the sidewall is coupled to an inlet in the door so that the liquid used to warm or cool the wall of the vessel can be used to warm or cool the door. In this way, an energy efficient warming and/or cooling can be provided for the door.

The double walls of the door and/or the wall may comprise vertical ribs in between the double walls that define open-ended channels. The ribs enable control of the flow of the liquid in between the double walls and facilitate that the liquid may flow in a regular manner and cover the whole desired area.

According to another embodiment, the door may comprise a heating film or blanket and the wall may comprise means to cool the vessel. This allows for optimization of robustness since the wall and the door have dedicated functions. Further, the heating film or blanket in the door may render the door more light-weight than the wall, and thus more easy to handle.

The invention further relates to a use of the mixing system as defined above for cultivating cells or microorganisms. The mixing system provides a flexible, efficient and safe cultivation process.

The above and further features and advantages of the invention are explained below in more detail with reference to the attached drawings.

BRIEF DESCRIPTION OF FIGURES

The present invention will be discussed in detail below with reference to the attached drawings. The embodiments shown in the figures are purely examples and should not be regarded as limiting the present invention in any way.

DETAILED DESCRIPTION

A vessel 1 according to one embodiment of the present invention is shown in FIGS. 1 to 4. The vessel 1 according to the present invention houses a disposable, transparent fluid mixing bag 2, e.g. a flexible bag of sterilizable plastic material, in which different kinds of fluids can be fermented or cultivated, and/or prepared. The vessel 1 and the bag 2 together are comprised in a mixing system of the present invention. The mixing system further comprises a mixer or a mixing arrangement, which can be of any suitable kind and is not object for the present invention and therefore not described in detail. Examples of suitable mixers are shown for example in US2011/0310696, which discloses an impeller assembly for mixing fluids inside the flexible bag. Further example is shown for example by U.S. Pat. No. 7,992,846, which shows a magnetic mixer coupled to the bottom of the flexible bag. The mixing system may further comprise, but is not limited to comprising, a sparger to deliver gas into the flexible bag, and the vessel and the bag may comprise probes and ports for different sensors. These further devices do not form a part of the inventive idea, are apparent to the skilled person and are therefore not explained more in detail in this context.

The size or volume of the mixing bags may vary from about 10 liters to about 2000 liters. The bags may have a size which is for example 20 liters, 50 liters, 200 liters, 500 liters or 1000 liters or 2000 liters. The disposable bags 2 preferably have a size and form that conforms to the size and form of the inner compartments of the vessel 1 so that the disposable bag 2 can be sufficiently supported by the vessel 1. The form may be different from the form of the inner compartment of the vessel as long as the walls of the mixing vessel provide sufficient support for the bag and so that no unnecessary folds in the bag will be formed. The disposable bags are preferably made of flexible, sterilizable plastic material, such as a polyethylene film. The bag is preferably transparent. Any plastic materials which are flexible and sterilizable may be used to form the disposable bag.

Figure 1:
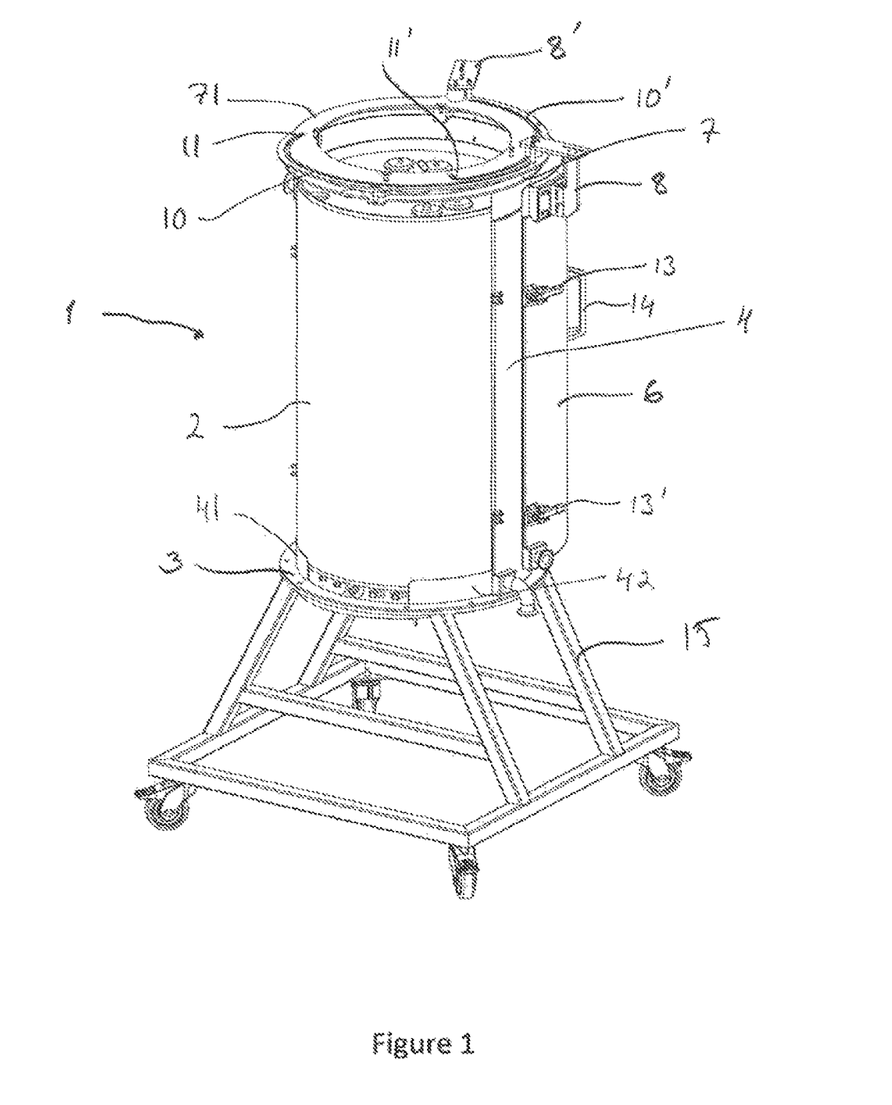
FIG. 1 schematically shows a perspective view of the vessel including a flexible bag according to a preferred embodiment of the present invention when the sliding door is in an open position.
Figure 2:
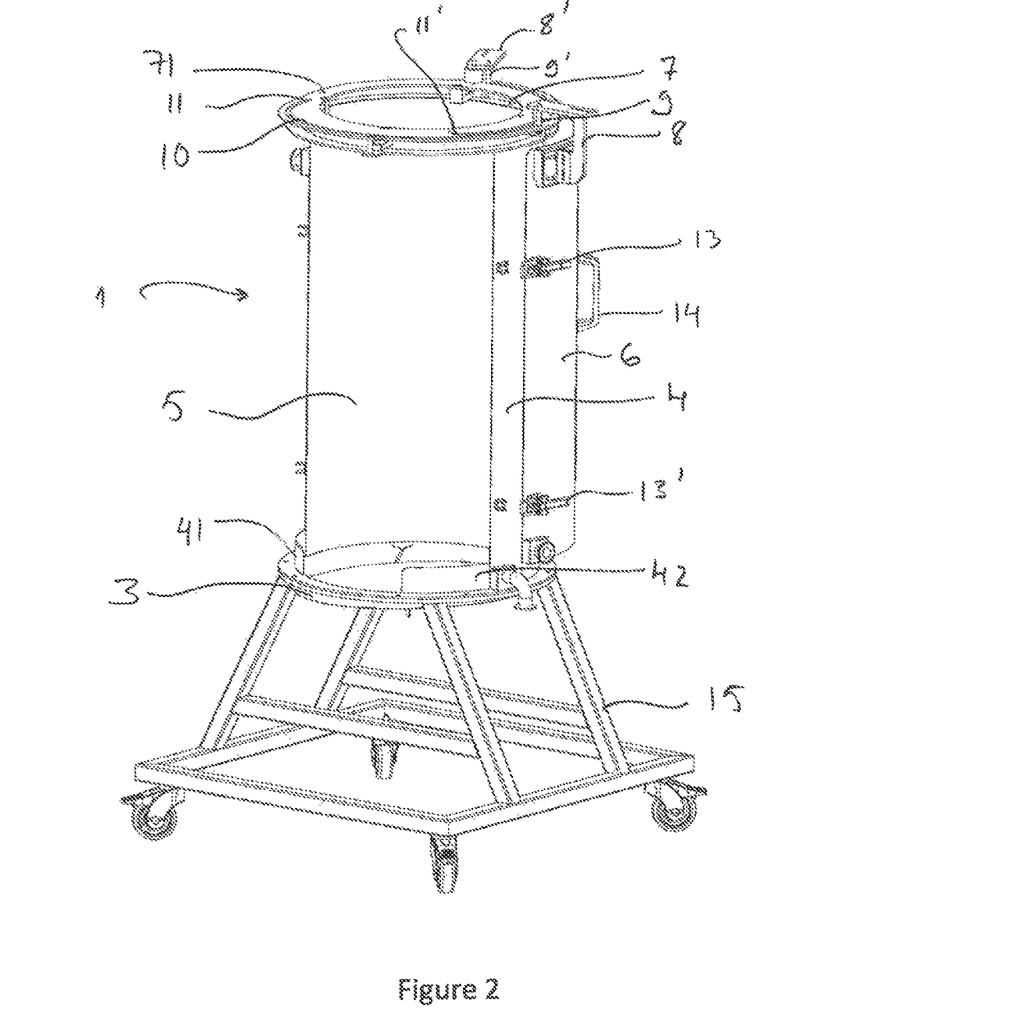
FIG. 2 schematically shows a perspective view of the vessel without a flexible bag according to a preferred embodiment of the present invention when the sliding door is in an open position FIG. 3 schematically shows a perspective view of the vessel according to FIG. 1 of the present invention when the sliding door is in a closed position.
Figure 3:
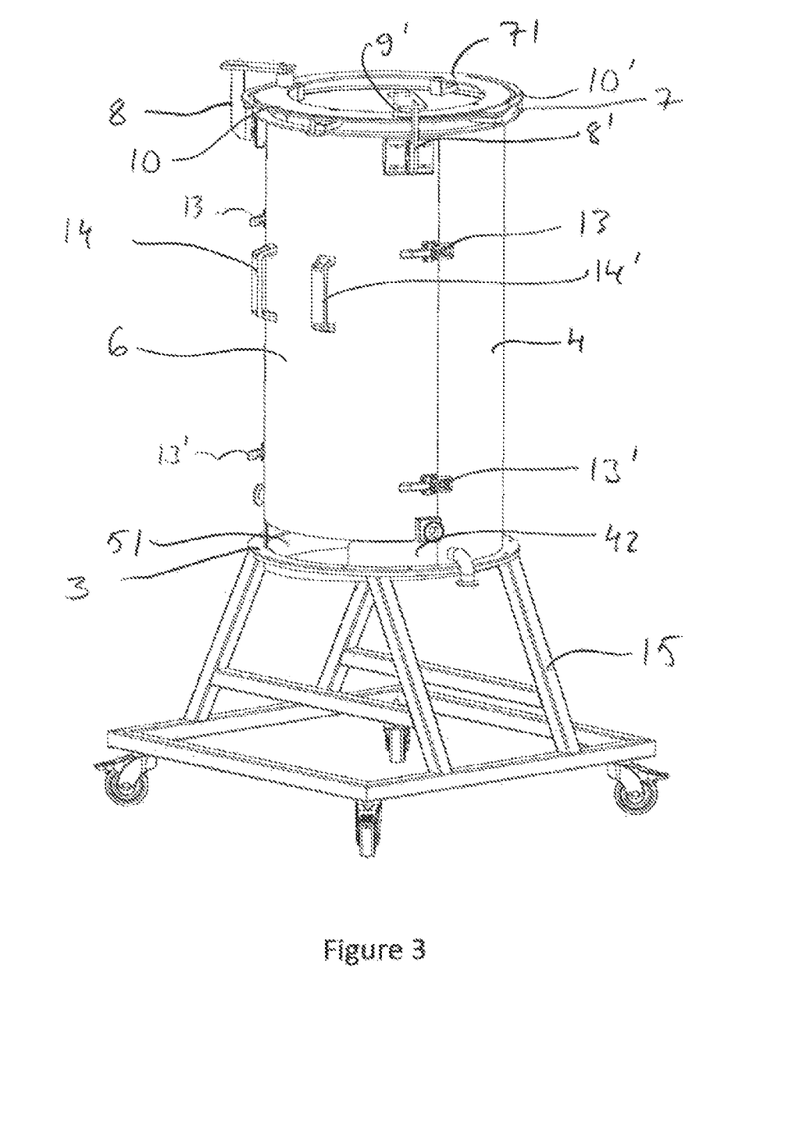
Figure 4:
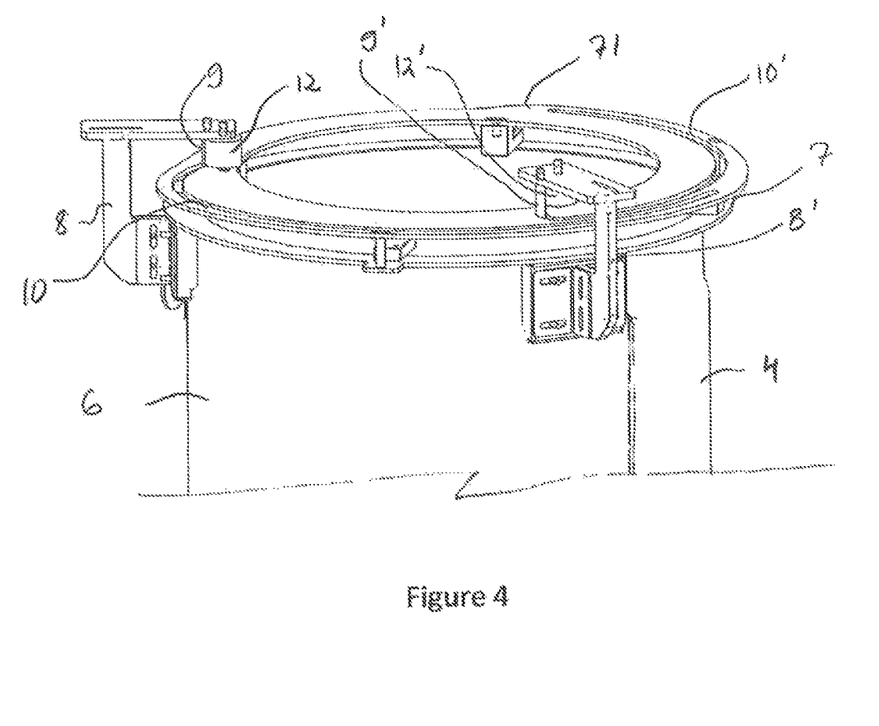
FIG. 4 schematically shows a cut, detailed side view of the upper part of the vessel according to FIG. 2 or 3.

With reference to FIGS. 1-3, the vessel 1 comprises a base 3 which supports the bag and a sidewall 4 extending vertically upwards from the base 3. The sidewall 4 comprises a door opening 5 (best shown in FIG. 2) which closable by a sliding door 6. In the FIGS. 1 to 3 it can be seen that the door opening extends through the whole height of the sidewall and the height of the door opening is 100% of the height of the side wall 4. The door opening 5 may be smaller and can have a height of at least 30%, such as at least 50% of the height of the sidewall 4 and is preferably at least 80% of the height of the sidewall, or alternatively 30-80% of the height of the sidewall. The bigger the opening the easier the access is inside the vessel, whereby an easy placement of the bag inside the vessel can be obtained. Particularly in larger vessels (e.g. of volume 200 L or above, such as 1000 L or above) there may however also be advantages in having a door with lower height, for mechanical stability reasons and in order to facilitate temperature control of the bioreactor. If the height of the door opening is less than 100% of the height of the vessel, the door opening may be located at any suitable position in the vessel in relation to the top and base of the vessel, e.g. in the middle of the vessel, in proximity of the top or in proximity of the base.

The mixing vessel 1 may be made of any material suitable for carrying and supporting the bag 2 including the fluid. The material is preferably dimensionally stable, such as metal, for example stainless steel. The material may also be plastic or glass. The material is preferably stainless steel. The vessel 1 can be made of combinations of different materials, e.g. the sidewall, or wall, 4 and/or the door 6 of the mixing vessel may be made of stainless steel, and vessel, the sidewall or the door thereof, may comprise a transparent window of glass or plastic so that the contents of the vessel can be inspected from the outside of the vessel. Preferably, the vessel 1 is made of a heat conducting material which enables the use of the vessel to heat or cool the fluid contents of the disposable bag. Therefore, the vessel is preferably made of principally stainless steel, except for some details in the vessel which may be of plastic or glass as mentioned above.

The door 6 in the FIGS. 1 to 3 does not cover the whole height of the door opening 5, whereby there is a gap 51 between the base 3 and the door 6 when the door is in its closed position, as best shown in FIG. 3. This makes it possible to place ports for necessary sensors or tubings on the side of the bag 2, as shown in FIG. 1. As shown in FIGS. 1 to 3, there are sleeves 41 and 42 coupled to the sidewall 4, which partly cover the lower part of the door opening 5. The sleeves 41 and 42 further support the flexible mixing bag 2 located inside the vessel 1. However, the sleeves could also be left out. The door 6 could cover the whole door opening 5 in its closed position. If the door covers the whole opening and the closure is made liquid tight, a secondary containment, which can contain liquids from the flexible bag for example in case of an accident, is also obtained. Preferably at least about 50% of the height of the door opening 5 is covered by the door 6 when the door 6 is in its closed position. Most preferably the door covers at least about 90% of the height of the door opening to ensure sufficient support for the mixing bag.

The door 6 covers the whole opening in the horizontal direction, i.e. the width of the door 6 is the same or substantially the same as the width of the opening 5. When the door is in its closed position, it is in the same plane with the remaining cylinder, wherein a substantially circular cylinder is formed. The door preferably covers about 30% of the cylinder mantle area, and can cover an area of from about 10% to about 50% of the mantle area.

The sliding door 6 is slidingly suspended to an upper part 7 of the vessel 1. The upper part is the side opposite to the base. In this context it is meant that the upper part 7 is the part of the vessel which covers less than 50% of the height of the vessel 1, starting from the topmost part, and most preferably less than 20% of the height of the vessel. The topmost part of the sidewall 4 could also include a top cover, e.g. a top plate, which is not shown in figures. A top plate could be included in the vessel to further protect the mixing bag 2 inside the vessel 1. However, in the embodiments shown in the figures, the vessel 1 has an open top and does not comprise a top plate. However, the embodiment shown in the figures could also include a top plate. The top plate could be removable or integrated to the sidewall 4. If the top plate is removable, an access to the inside of the vessel could be further facilitated. However, an integrated top plate could improve the mechanical stability of the vessel.

The vessel 1 shown in the FIGS. 1 to 4 is circular cylinder, also called right circular cylinder, when the door is in its closed position. This makes the door 6 easy to manufacture, since the door may have substantially the same radius as the sidewall 4 or mantle in the remaining cylinder. The door 6 may be manufactured of the same material as the sidewall 4 of the vessel, i.e. the door may be made of hard material, since no flexibility is required to adapt the door to the remaining vessel when the door is in its open position which would be needed if the vessel was e.g. elliptic cylinder.

The upper part 7 of the vessel 1 comprises an upper annular element 71 to which the door 6 is slidingly suspended. Preferably, the annular element 71 is placed on top of the topmost part of the sidewall 4. The annular element 71 is manufactured of a durable, dimensionally stable material, which is able to carry the weight of the door 6.

As shown in the FIGS. 1 to 4, the door 6 comprises suspension means 8, 8' to suspend the door 6 on the annular element 71. The suspension means 8, 8', respectively, comprise a guiding element in the form of a pin 9, 9', as shown best in FIG. 4, which slides in tracks 10, 10'. The tracks in the figures are through holes, but instead of a through hole arrangement, rails which define a channel, which guide a guiding element, could be used. The guiding element could also be a pin arrangement with a rotating shell or for example a ball bearing to facilitate the sliding in the track or rail of the annular element. Through this structure, a simple and a reliable sliding arrangement for the door is obtained. The sliding movement can be further improved by including sliding elements 12, 12', respectively, comprising a ball bearing which is arranged to slide outside the track or rail 10, 10' in the suspension means 8, 8', as shown in FIG. 3. The upper annular element 71 may comprise a recess in which the ball bearing of the sliding elements 12, 12' can be at least partially accommodated when the door is in its closed position.

In other embodiments the door could also be suspended to the upper part 7 in other ways. For example, the upper part 7 of the vessel 1 could comprise an annular flange, which could be arranged below the topmost part of the vessel. The flange could comprise tracks or rails in a similar way as explained above, and the door could comprise suspension means in a similar way as explained above to suspend the door slidingly to the vessel.

If the door is heavy, e.g. in case of a large mixing vessel, the door can comprise more than two suspension means. However, the amount of the tracks or rails corresponds to the amount of suspension means to enable the sliding movement of the door. Also, if the door is light such as in small vessels, only one suspension means could be sufficient. In the embodiment shown in the FIGS. 1 to 4 there are two suspension means and the upper annular element 7 comprises a track 10, 10' or a rail for each of the suspension means 8, 8'.

To enable a radial displacement of the door outwards in relation to vessels diametrical center when the door is to be opened from its closed position, i.e. the position in which the door 6 covers the width of the door opening 5 and is in the same circular plane as the sidewall 4 and forms a circular cylinder in cross section together with the side wall 4, the tracks 10, 10' comprise an arcuate end portion 11, 11' which is closer to the diametrical center of the vessel 1 than the remaining portion of the track 10, 10'. This makes it possible when the door 6 is opened from its closed position that the door 6 moves radially outwards from the diametrical center of the vessel so that it becomes free from contact with the remaining wall 4 of the vessel 1.

The radial movement could be arranged in other ways as well. For example the suspension means could comprise a hinged arm that could turn the door towards the diametrical center when the door is to be closed so that the door comes into contact with the sidewall.

The base 3 of the vessel 1 may comprise a lower annular element, which is not shown in the figures, having a similar structure as the upper annular element. The lower annular element preferably also comprises one track or rail for one suspension means. The door 6 comprises similar suspension means as the suspension means 8, 8' also in the lower part of the door. The number of the lower suspension means could be the same as the amount of the upper suspension means 8, 8', but also only one suspension means could be used. The lower suspension means provide further stability for the door and improved sliding movement.

In FIGS. 1 to 3 the door comprises handles 14, 14', which can be used to push the door when the door is opened or closed. The door is operated manually in the examples shown in the figures, but could of course be automated in any suitable way.

The vessel preferably comprises locking means 13, 13' to lock the sliding door 6 when the door is in its closed position. Any suitable locking means known in the art may be used, for example clamp-type fasteners.

The sliding door 6 together with the locking means 13, 13' provide a safe construction for the mixing vessel. For example, even if the locking means would be accidentally opened during the use of the mixing vessel, the sliding door stays in place and supports the flexible bag in the reactor. In case of a conventional hinged door there is a risk that if the door opened accidentally during the operation, the bag would not be supported in a sufficient manner and could fall down and get damaged with catastrophic consequences. With the sliding door of the present invention this risk is significantly decreased.

Also, the sidewall 4 of the vessel 1 may comprise fastening means inside the vessel 1, such as clamp holders, (not shown in the figures) to secure the mixing bag 2 to the vessel 1.

The mixing system shown in FIGS. 1 to 3 is supported by a frame structure 15 with wheels to enable easy movement of the system.

The door 6 may comprise a double-wall structure (not shown in the figures) wherein a heated or cooled liquid can be arranged to flow between the double walls to warm or cool, respectively, the vessel and thereby the fluid carried by the mixing bag 2. Also the sidewall 4 of the vessel 1 may comprise double-wall structure, wherein a heated or cooled liquid is arranged to flow between the double walls to warm or cool the vessel and there through the fluid carried by the mixing bag 2.

The door and/or the sidewall may comprise vertical ribs in between the double walls (not shown in the figures), so that the flow of the liquid inside the double wall can be controlled. The height of the ribs is preferably less than 80% of the height of the door and/or the sidewall, and the ribs are arranged at a distance of from about 5-50 cm. The ribs define open-ended channels so that the liquid may flow in a regular manner and cover the whole desired area.

To further improve the energy-efficiency of the warming and/or cooling of the vessel, the sidewall 4 of the vessel 1 comprises an inlet and outlet for the liquid, and the door 6 comprises an inlet and an outlet for the liquid, wherein the outlet of the liquid from the sidewall 4 is coupled by means of a flexible hose to an inlet in the door 6 so that the liquid used to warm or cool the sidewall 4 of the vessel 1 can be used to warm or cool the door 6. The flexible hose follows the movement of the sliding door in an easy way.

According to another embodiment, the door 6 may comprise a heating film or blanket (not shown in the figures) and the wall 4 may comprise means to cool the vessel, e.g. cooling blanket, or double walls comprising cooling liquid in between the walls as defined above. This allows for optimization of robustness since the wall and the door have dedicated functions. The door and the wall could also have same functions, i.e. to cool or heat the door and the wall, respectively. The heating film or blanket in the door renders the door 6 more light-weight, and thus more easy to handle.

The mixing system according to the present invention can be used for cultivating cells or microorganisms. Before the cultivation begins, the mixing bag, which is sterilized and folded, is placed inside the vessel 1. The bag is then filled with sterile gas to open the bag in a sterile manner. Thereafter, the bag is filled with a liquid and the cultivation of the cells and/or microorganisms may be initiated. The system provides a safe and easy way to use disposable system.

The present invention may be varied within the scope of the appended claims.

The invention claimed is:

1. A mixing system, comprising:
   a vessel having an annular upper portion;
   a door configured for connection to the annular upper portion; and
   a suspension device (i) having one end slidably connected to the annular upper portion and another end connected to the door and (ii) configured for moving the door about the annular upper portion in a suspended manner.

2. The mixing system according to claim 1, wherein the vessel further comprises:
   a disposable fluid mixing bag;
   a base supporting the fluid mixing bag; and
   a side wall extending vertically upwards from the base;
   wherein the sidewall comprises a door opening made closable by the door.

3. The mixing system according to claim 2, wherein the door opening has a height of at least 30-100% of the height of the sidewall.

4. The mixing system according to claim 1, wherein the vessel is a circular cylinder when the door is in its closed position and the annular upper portion of the vessel comprises an upper annular element to which the door is sliding suspended.

5. The mixing system according to claim 4, wherein the suspension device comprises a guiding element for slidably suspending the door to the annular upper element.

6. The mixing system according to claim 5, wherein the upper annular element comprises a track or a rail by which the guiding element can slide.

7. The mixing system according to claim 5, wherein the guiding element is a pin.

8. The mixing system according to claim 5, wherein the door comprises a suspension device on both sides of the door and wherein the upper annular element comprises a track or a rail for each of the suspension device.

9. The mixing system according to claim 6, wherein the track or rail comprises an arcuate end portion which is closer to the diametrical center of the vessel than the remaining portion of the track or rail, wherein, when the door is opened from its closed position, the door moves radially outwards in relation to the diametrical center of the vessel so that it becomes free from contact with a remaining wall of the vessel.

10. The mixing system according to claim 6, wherein the suspension device comprises a sliding element comprising a ball bearing which is configured to slide outside the track or rail.

11. The mixing system according to claim 10, wherein the upper annular element comprises a recess in which the ball bearing of the sliding element is at least partially accommodated when the door is a closed position.

12. The mixing system according to claim 2, wherein the door comprises a lower suspension device, and a lower portion of the sidewall comprises a lower annular element comprising at least one track or rail to guide the lower suspension device comprising a guiding element or slidably suspending the door to the lower annular element.

13. The mixing system according to claim 12, wherein the vessel comprises a locking device to lock the door when the door is in its closed position.

14. The mixing system according to claim 13, wherein the upper portion of the sidewall of the vessel comprises a fastening device to secure the mixing bag to the vessel.

15. The mixing system according to claim 14, wherein the door comprises double walls, and wherein a heated or cooled liquid is arranged to flow between the double walls to warm or cool the vessel.

16. The mixing system according to claim 15, wherein the sidewall of the vessel comprises double walls, and wherein a heated or cooled liquid is arranged to flow between the double walls to warm or cool the vessel.

17. The mixing system according to claim 16, wherein the wall of the vessel comprises an inlet and outlet for the liquid, and wherein the door comprises an inlet and an outlet for the liquid, wherein the outlet of the liquid is coupled to an inlet in the door so that the liquid used to warm or cool the wall of the vessel can be used to warm or cool the door.

18. The mixing system according to claim 16, wherein the double walls of the door and/or the wall comprise vertical ribs in between the double walls that define open-ended channels.

19. The mixing system according to claim 18, wherein the door comprises a heating film or blanket, and the wall comprises a device to cool the vessel.

* * * * *